(12) United States Patent
Amin et al.

(10) Patent No.: US 9,006,488 B1
(45) Date of Patent: Apr. 14, 2015

(54) SOLVENT FREE SYNTHESIS OF ACETAMINOPHEN

(71) Applicants: Muhammad Amin, Sargodha (PK); Muhammad S. Iqbal, Lahore (PK)

(72) Inventors: Muhammad Amin, Sargodha (PK); Muhammad S. Iqbal, Lahore (PK)

(*) Notice: Subject to any disclaimer, the term of this patent is extended or adjusted under 35 U.S.C. 154(b) by 0 days.

(21) Appl. No.: 14/221,031

(22) Filed: Mar. 20, 2014

(51) Int. Cl.
*C07C 231/02* (2006.01)

(52) U.S. Cl.
CPC .................................... *C07C 231/02* (2013.01)

(58) Field of Classification Search
CPC .................................................... C07C 231/02
USPC ......................................... 564/134, 142, 144
See application file for complete search history.

(56) References Cited

U.S. PATENT DOCUMENTS

| | | | | |
|---|---|---|---|---|
| 6,634,576 | B2 * | 10/2003 | Verhoff et al. | 241/21 |
| 6,969,775 | B2 * | 11/2005 | Bhattacharya et al. | 564/223 |
| 8,691,975 | B2 * | 4/2014 | Tapsak | 536/119 |
| 2002/0047058 | A1 * | 4/2002 | Verhoff et al. | 241/26 |
| 2009/0124680 | A1 * | 5/2009 | Yoo et al. | 514/397 |
| 2011/0009372 | A1 * | 1/2011 | Frincke | 514/170 |

OTHER PUBLICATIONS

Sharma et al, Inorganic and Organometallic Polymers and Materials, 2010, 20(4), 698-705.*
Farhadi et al, Applied Catalysis, A, General: 2010, 382(2), 293-302.*
Satam et al, Catalysis Communications, 2008, 9(14), 2365-2370.*
Satam et al, Synthetic Communications, 2007, 37(17), 3011-3020.*

* cited by examiner

*Primary Examiner* — Shailendra Kumar
(74) *Attorney, Agent, or Firm* — Sarfaraz Niazi

(57) ABSTRACT

A solvent-free mechanical process of reacting amine compounds with acetylating agents resulting in amides such as acetaminophen is described.

5 Claims, 4 Drawing Sheets

SOLVENT FREE SYNTHESIS OF ACETAMINOPHEN

FIELD OF THE INVENTION

The invention relates to the synthesis of acetaminophen, a widely used active pharmaceutical ingredient in analgesic and antipyretic formulations.

BACKGROUND OF THE INVENTION

Acetaminophen, also commonly known as paracetamol, is a widely used active pharmaceutical ingredient. Its world demand is around 100,000 metric tons including more than 50% demand in United States of America. Acetaminophen is being prepared by Celanese, Mallinckrodt, Monsanto, and Sterling processes.

In the Celanese process, as described in U.S. Pat. No. 4,954,652, cited herein as a reference, acetaminophen is prepared by Beckman rearrangement of 4-hydroxyacetophenone oxime in an alkyl alkanoate as a solvent in the presence of a catalyst. The other three processes involve N-acetylation of 4-aminophenol with acetic anhydride in an inert solvent such as water, water-isopropanol mixture, acetic acid, ethylacetate, benzene and other suitable hydrocarbons. 4-Aminophenol is also extensively used for other applications such as in hair dye formulations, as rubber additive and in photographic developing agents, and is, therefore, being produced by several manufacturers across the world.

Thus, most of the manufacturers of acetaminophen use 4-aminophenol as the most commonly available starting material. Over the past decade significant efforts have been made to make chemical manufacturing environmentally friendly through the green chemistry approach. Attempts also have been made to minimize or eliminate the use of solvents in the manufacture of acetaminophen. For example, a solvent-minimized synthesis from 4-nitrophenol has been described in U.S. Pat. No. 6,969,775 B2, but this process employs still some undesirable reagents, Triton X-405 (a polyoxyethylene ether) and potassium thioacetate, as the catalyst system, which may end up in the product.

These materials or their degradation products can present a hazard if present as impurities in the product or as pollutants in the environment. On account of very high consumption of acetaminophen a more clean and economical process is needed for its production. Until now, there exists no cleaner method for the synthesis of acetaminophen than that disclosed in the present invention.

SUMMARY OF THE INVENTION

The present invention deals with a process for the manufacture of N-acetyl aminophenols. This invention provides the cleanest and most economical method for the synthesis of the most prescribed analgesic acetaminophen. The method excludes the use of any catalyst or solvent and involves the reaction of only two basic materials, namely 4-aminophenol and acetic anhydride or acetyl chloride. The two reactants are brought in contact and allowed to react by mixing and mechanical grinding in a pestle mortar. The process is called mechanochemical synthesis.

By this process, N-acetylation of amines having formula $R_1$—$NHR_2$, where $R_1$=an alkyl or aryl group and $R_2$=H, an alkyl or aryl group, can be achieved. In a preferred embodiment acetaminophen can be produced in a solvent-free environment. Acetaminophen is produced in high yield, with pharmaceutically acceptable quality, by one-step-one-pot method. The process described in the present invention provides with a shortest route for synthesis of acetaminophen using commonly available inexpensive chemicals 4-aminophenol and acetic anhydride or acetyl chloride. The acetylation reaction affording acetaminophen in >95% yield can be completed in less than 15 min. The process of the invention can also be used to produce other useful N-acetylated products or intermediates.

BRIEF DESCRIPTION OF THE DRAWINGS

FIG. 2 depicts UV-visible spectra of reference standard and sample from product of Example 4.

DETAILED DESCRIPTION OF THE INVENTION

Figure 1A:
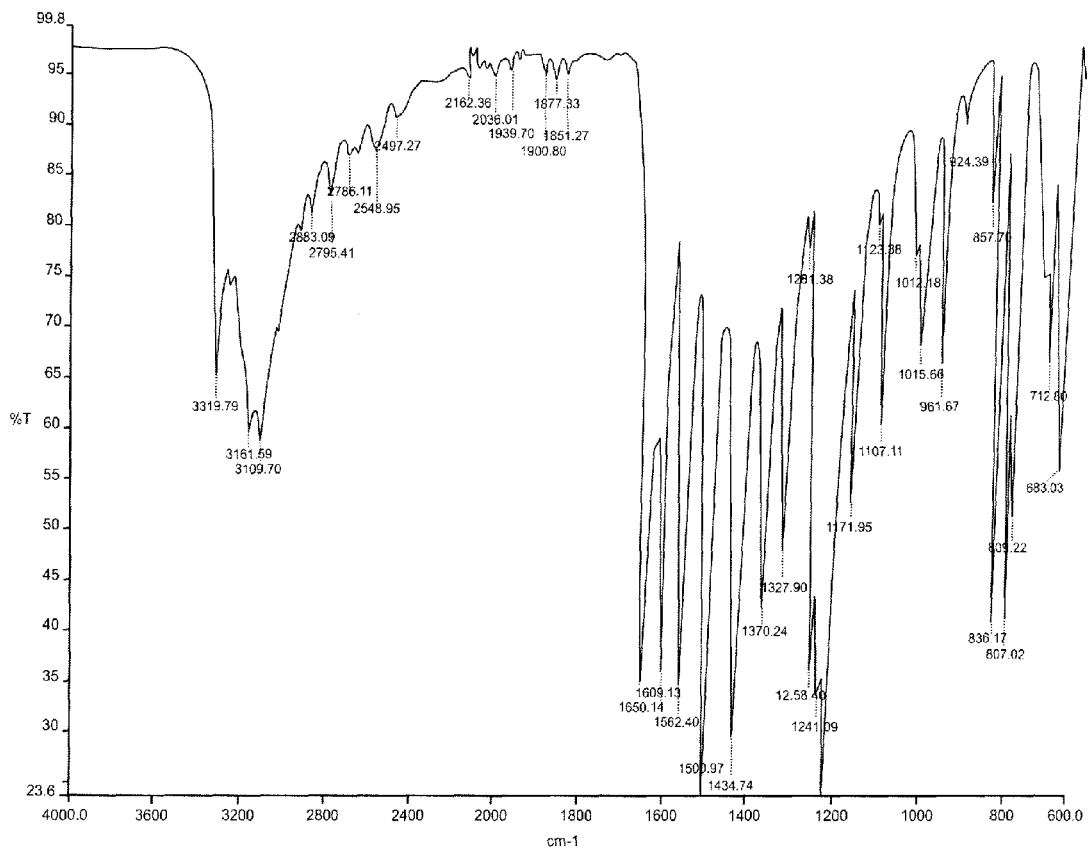
FIGS. 1A and 1B depict FT-IR Spectra of reference standard (1A) and sample (1B) from product of Example 4.

The invention provides a solvent-free and catalyst-free method for producing acetaminophen, which has been previously made by several processes by use of a solvent and/or a catalyst. In one aspect of the invention, the process employs 4-aminophenol and acetic anhydride as the starting materials which are mixed together in equimolar quantities and ground vigorously in a pestle mortar for sufficient time to ensure thorough contact of the reactants particles. After grinding operation the desired product is obtained which is dried under vacuum at about 40° C. In another aspect of the invention, 4-aminophenol is mixed with acetyl chloride in equimolar quantities and processed in the same manner. The products obtained by these processes are identical and pass the BP and USP tests prescribed for acetaminophen.

In another aspect of the invention, the grinding operation by use of pestle and mortar can be replaced advantageously by any other mechanical grinding/milling system such as a ball mill equipped with an exhaust system for collection of fumes and vapors. In this way the process is easily scaled up for commercial production of the product. Ball mills, equipped with suitable feed and exhaust systems, having capacity above 1500 kg are available commercially.

During the process of grinding/milling fumes/vapors of acetic acid are released which can be safely collected by scrubbing the emissions through water. This process requires the purity of 4-aminophenol and acetic anhydride or acetyl chloride to be 98% minimum, which is normally available commercially.

The product obtained through the process of this invention has the following attributes:

a. It possesses very small particle size. By virtue of this quality the product is suitable for formulation of suspensions, syrups and tablets.

b. It is absolutely free from impurities, such as N-(4-hydroxyphenyl)propanamide, N-phenylacetamide, 4-(acetylamino)phenyl acetate as mentioned in British Pharmacopeia 2009, N-(2-hydroxyphenyl)acetamide (R. N. Rao and A. Narasaraju in Analytical Sciences vol 22, page 287, 2006) benzoquinoimines (EP 2 100 596 A2, Application No. 09161268.9, dated Sep. 16, 2009), which are generated under the conditions of high temperature and acidic pH in solvent-based processes and may be present in the product thus manufactured.

The use of the method of the present invention eliminates the use of heating required in solvent-based methods. It further eliminates the use of special reactor materials required due to corrosive nature of process materials involved in the solvent-based methods.

The solvent-free method of amidation presented in the present invention can be successfully extended to other amino compounds of interest.

The following are the non-limiting examples, which illustrate the solvent-free amidation of 4-aminophenol with acetic anhydride and acetyl chloride.

EXAMPLES

Example 1

Synthesis of acetaminophen by use of acetic anhydride: 0.1 Mole (10.913 g) of 98% pure 4-aminophenol and 0.1 mole (10.209 g) of 99% pure acetic anhydride were transferred to a 6 inch mortar. A slight excess amount (0.100 g) of acetic anhydride was added to this mixture. The mixture was first mixed gently then ground vigorously by use of a pestle under a fume cupboard.

Example 2

Synthesis of acetaminophen by use of acetyl chloride: 0.1 Mole (10.913 g) of 98% pure 4-aminophenol and 0.1 mole (7.85 g) of 99% pure acetyl chloride were transferred to a 6 inch mortar. A slight excess amount (0.100 g) of acetyl chloride was added to this mixture. The mixture was first mixed gently then ground vigorously by use of a pestle under a fume cupboard.

Example 3

Preparation of acetaminophen by use of acetic anhydride in a ball mill: One hundred moles (10.913 kg) of 98% pure 4-aminophenol and 100 moles (10.209 kg) of 99% pure acetic anhydride were transferred to a rotary stainless steel ball mill equipped with an exhaust and a scrubber system. A slight excess amount (0.100 kg) of acetic anhydride was added to this mixture. The mixture was first mixed gently then ground to about 10 μm particle size. Yield: 14.6 kg.

Example 4

Preparation of acetaminophen by use of acetyl chloride in a ball mill: One hundred moles (10.913 kg) of 98% pure 4-aminophenol and 100 moles (7.85 kg) of 99% pure acetyl chloride were transferred to a rotary stainless steel ball mill equipped with an exhaust and a scrubber system. A slight excess amount (0.100 kg) of acetyl chloride was added to this mixture. The mixture was first mixed gently then ground to about 10 μm particle size. Yield: 14.9 kg.

Example 5

The products obtained from Examples 1-4 were tested according to United States Pharmacopoeia 30 and British Pharmacopoeia 2009; the results thereof are given in Table 1.

TABLE 1

| Test | USP Specification | BP Specification | Typical experimental value |
| --- | --- | --- | --- |
| Appearance | | White crystalline powder | White crystalline powder |
| Solubility | | Sparingly soluble in water, freely soluble in alcohol, very slightly soluble in methylene chloride | Sparingly soluble in water, freely soluble in alcohol, very slightly soluble in methylene chloride |
| Identification | Conforms to the specifications | Conforms to the specifications | Conforms to the specifications |
| Related substances | | Conforms to the specifications | Conforms to the specifications |
| Loss on drying | | 0.5% at 100-105° C. | 0.3-0.4% at 105° C. |
| Sulphated ash | | Maximum 0.1% | 0.2-0.04% |
| Melting range | 168-172° C. | 168-172° C. | 171-172° C. |
| Water | Not more than 0.5% | | 0.3-0.4% |
| Residue on ignition | Not more than 0.1% | | 0.04-0.06% |
| Chloride | Not more than 0.014% | | Less than 0.14% |
| Sulfate | Not more than 0.02% | | Meets the requirement |
| Sulfide | Meets the requirement | | Meets the requirement |
| Heavy metals | Not more than 0.001% | | Meets the requirement |
| Free p-aminophenol | Not more than 0.005% | Not more than 50 ppm | 0.003-0.004% |
| Limit of p-chloroacetanilide | Not more than 0.001% | Not more than 10 ppm | 0.0004-0.0006% |
| Readily carbonizable substances | Meets the requirement | | Meets the requirement |
| Organic volatile impurities | Meets the requirements | | Meets the requirements |
| Assay | 98-101% on dry substance basis | 99-101% on dry substance basis | 99-100% |

TABLE 2

| Element | Theoretical (%) | Product of Example 1 | Product of Example 2 | Product of Example 3 | Product of Example 4 |
| --- | --- | --- | --- | --- | --- |
| C | 63.56 | 63.68 | 63.51 | 63.62 | 63.65 |
| H | 6.00 | 6.04 | 6.00 | 6.13 | 6.07 |
| N | 9.27 | 9.40 | 9.25 | 9.30 | 9.19 |

Figure 1B:
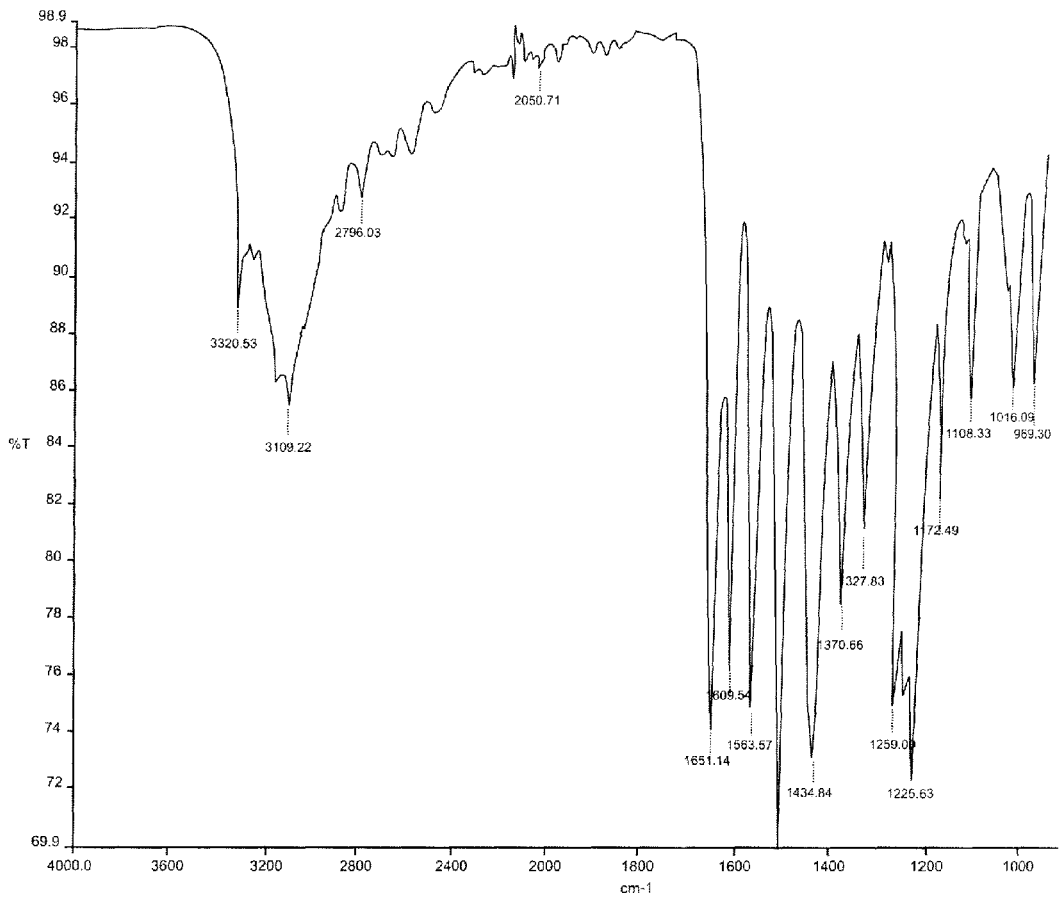
Figure 3A:
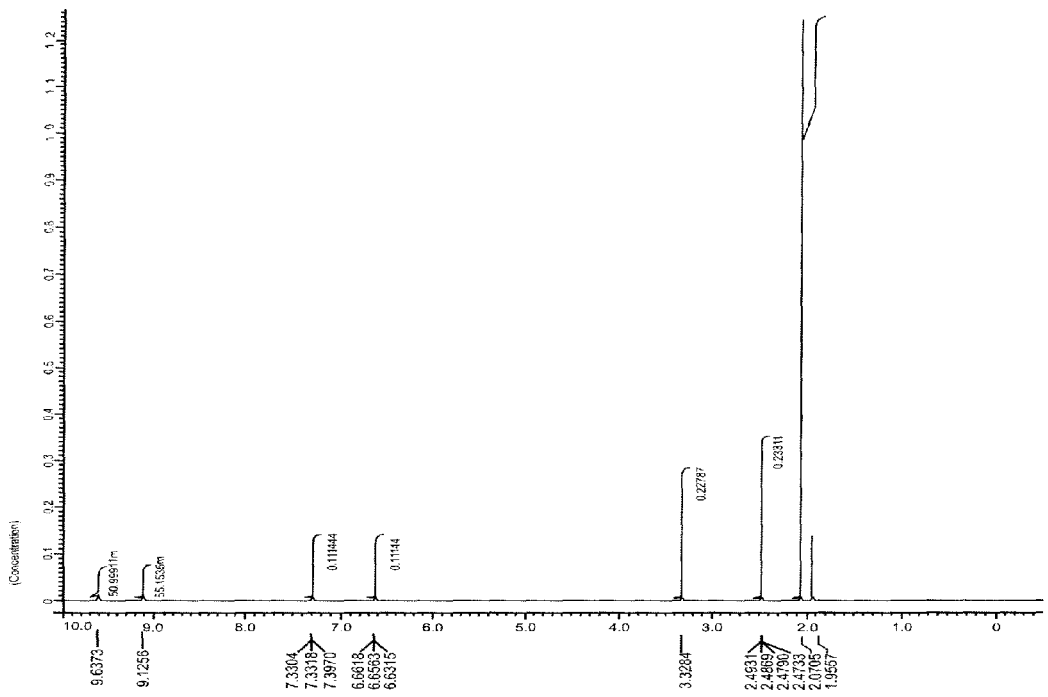
FIGS. 3A and 3B depict HNMR Spectra of reference standard (3A) and sample (3B) from product of Example 4
Figure 3B:
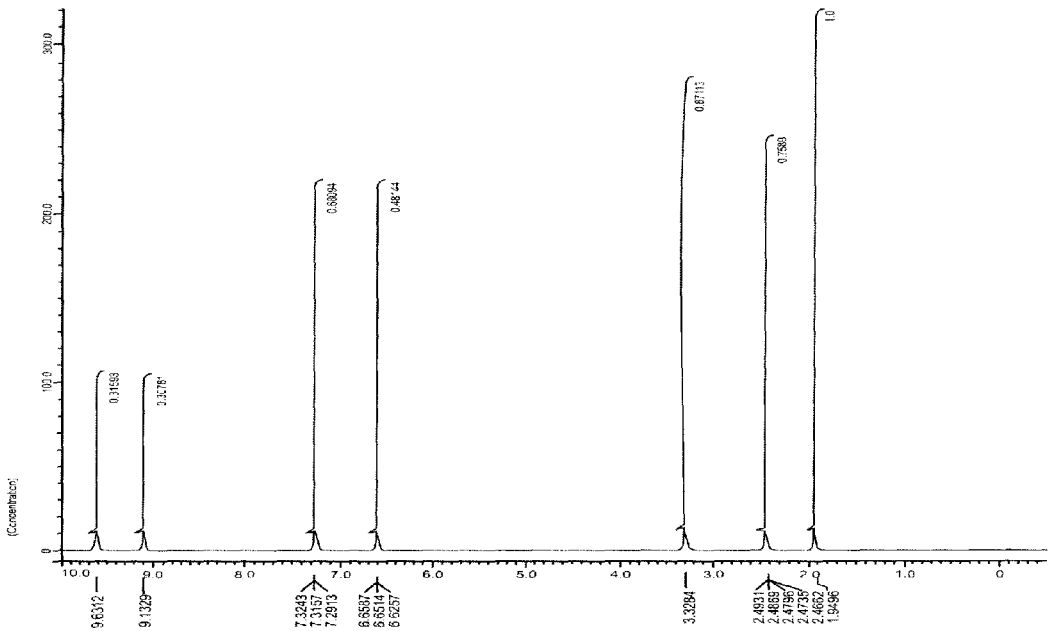
Figure 4:
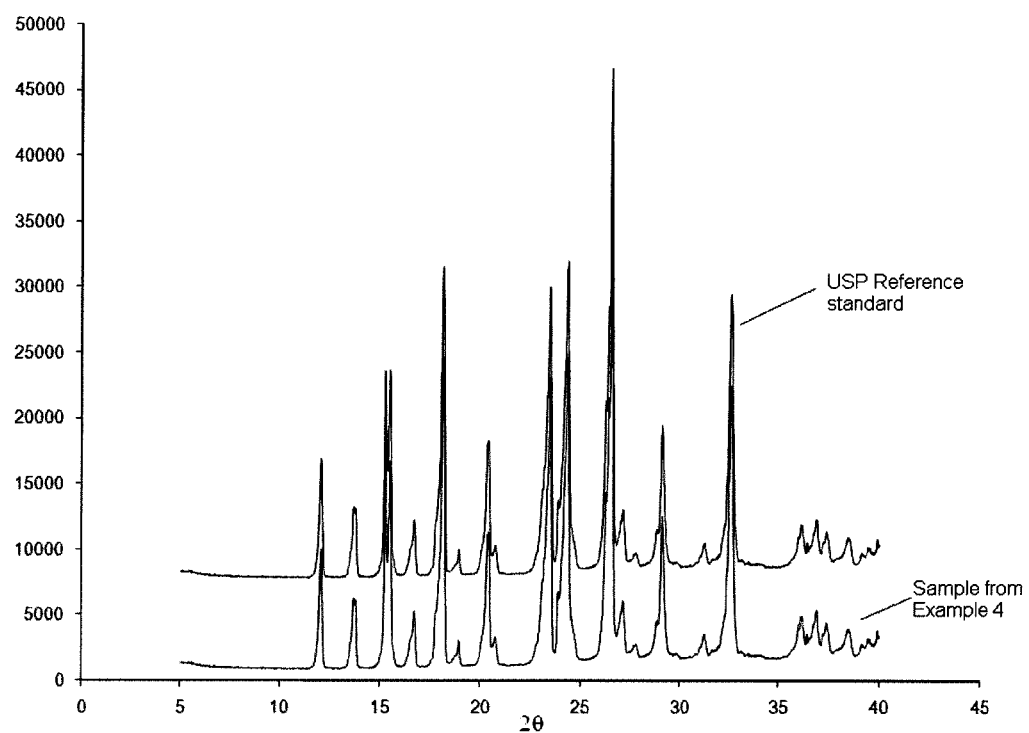
FIG. 4 depicts powder XRD spectra of reference standard and sample from product of Example 4

The products were characterized by use of elemental (CHN) analysis, FT-IR, UV-Visible (diffuse reflectance), $^1$HNMR and powder XRD techniques. The elemental analysis agreed, within 0.4%, with the theoretical composition as shown in Table 2. The FT-IR, UV-Visible (diffuse reflectance), $^1$HNMR and powder XRD spectra of the products of Examples 1-4 matched with the spectrum of USP reference standard of acetaminophen. Typical spectra are shown in FIGS. 1-4. The powder XRD confirms the crystalline nature of the products.

What is claimed is:

1. A method of acetylating an amine compound by grinding it under a mechanical shear force with acetic anhydride or acetyl chloride.

2. The method of claim 1, wherein the amine is 4-acetaminopenol.

3. The method of claim 2, wherein the final product is acetaminophen.

4. The method of claim 2, wherein 4-acetaminophenol and the acetic anhydride or acetyl chloride are present in a 1:1 molar ratio.

5. The method of claim 1, wherein the shear force is applied using a pest-mortar, a ball mill, or a planetary mill.

* * * * *